US005676145A

United States Patent [19]

Bar-Lavie

[11] Patent Number: 5,676,145
[45] Date of Patent: Oct. 14, 1997

[54] CEREBRAL HEMODYNAMIC MONITORING SYSTEM

[75] Inventor: Yaron P. Bar-Lavie, Baltimore, Md.

[73] Assignee: University of Maryland at Baltimore, Baltimore, Md.

[21] Appl. No.: 517,356

[22] Filed: Aug. 21, 1995

[51] Int. Cl.⁶ ..................................................... A61B 5/00
[52] U.S. Cl. ........................ 128/634; 128/642; 128/664; 128/691; 128/736
[58] Field of Search ............................ 128/634, 664–665, 128/691–692, 670, 642, 736; 604/53; 606/41

[56] References Cited

U.S. PATENT DOCUMENTS

| 4,217,910 | 8/1980 | Khalil | 128/670 |
| 4,949,724 | 8/1990 | Mahutte et al. | |
| 5,357,954 | 10/1994 | Shigezawa et al. | 128/634 |
| 5,429,131 | 7/1995 | Scheinman et al. | 606/41 X |

OTHER PUBLICATIONS

Gotoh et al. "Continuous Recording of Human Cerebral Blood Flow and Metabolism", *Medical Research Engineering*, 1966.

Gotoh et al. "Continuous Recording of Human Cerebral Blood Flow (pp. 13–19) and Metabolism" *Medical Research Engineering*, 1966.

Julio Cruz et al., "Continuous Monitoring of Cerebral Oxygenation in Acute Brain Injury: Multivariate Assessment of Severe Intracranial 'Plateau' Wave—Case Report", *The Journal of Trauma* (1992) 32:401–403.

Donald Baim, et al., "Improved Catheter for Regional Coronary Sinus Flow and Metabolic Studies", *The American Journal of Cardiology* (1980) 46:997–1000.

J. Berré, "Bedside Estimation of Cerebral Blood Flow" *Yearbook of Intensive Care and Emergency Medicine 1994* (1994) pp. 646–654.

Julio Cruz et al., "Cerebral Blood Flow, Vascular Resistance, and Oxygen Metabolism in Acute Brain Trauma: Redefining the Role of Cerebral Perfusion Pressure?" *Critical Care Medicine* (1995) 23:1412–1417.

(List continued on next page.)

Primary Examiner—Lee S. Cohen
Assistant Examiner—Ryan Carter
Attorney, Agent, or Firm—Burns, Doane, Swecker & Mathis, L.L.P.

[57] ABSTRACT

A cerebral hemodynamics monitoring device includes a catheter having an optic fiber 20 for measurement of oxygen saturation, a first thermistor 30 positioned not more than about 25 mm from the tip of the catheter, and a second thermistor 32, located preferably at an entry to the catheter. The catheter is insertable in a vein over a guide wire using the Seldinger technique. The monitoring device also includes a computerized cerebral hemodynamics monitor that performs continuous jugular oximetry ($S_jO_2$, %), arterial pulse oximetry ($S_aO_2$, %), and measurement of jugular blood flow (JBF, ml/min/100 g tissue), preferably via retrograde thermodilution based on data collected in the catheter devices. Based on these measurements, the monitoring device performs continuous calculation of cerebral $O_2$ extraction ($CEO_2$, %), cerebral $O_2$ consumption ($CMRO_2$), cerebral blood flow (CBF), and cerebral vascular resistance (CVR). The device system also includes a programmable injectate infusion pump connected to the catheter that provides for background flow, planned interval boluses, and PRN bolus capability. The monitoring system also includes output devices for displaying data and for communicating data to other external devices.

22 Claims, 1 Drawing Sheet

OTHER PUBLICATIONS

Julio Cruz et al., "Continuous Monitoring of Cerebral Oxygenation in Acute Brain Injury: injection of Mannitol During Hyperventilation", *J. Neurosurg.* (1990) 73:725–730.

Michael Scheinberg et al., "Continuous Monitoring of Jugular Venous Oxygen Saturation in Head–Injured Patients", *J. Neurosurg.* (1992) 76:212–217.

M. Lagerkranser et al., "Cerebral Blood Flow and Metabolism During Adenosine–Induced Hypotension in Patients Undergoing Cerebral Aneurysm Surgery", *Acta Anaesthesiol Scand* (1989) 33:15–20.

C. Robertson et al., "Cerebral Blood Flow, Arteriovenous Oxygen Difference, and Outcome in Head Injured Patients", *Journal of Neurology, Neurosurgery, and Psychiatry* (1992) 55:594–603.

Karen March, "Retrograde Jugular Catheter: Monitoring $SjO^2$" *Journal of Neuroscience Nursing* (1994) 26:48–51.

C. De Deyne et al., "New Insights in the Management of Acute Neurologic Crises Using Jugular Bulb Oximetry", 1994 Yearbook of Intensive Care and Emergency Medicine, 638–644.

J. van der Linden et al., "Transcranial Doppler–estimated versus Thermodilution–estimated Cerebral Blood Flow During Cardiac Operations", (1991) *J Thorac Cardiovasc Surg* 102:95–102.

J Douglas Miller, "Swelling and Blood Flow in the Injured Child's Brain" *The Lancet* (1994) 344 421–422.

Jurg Jaggi et al., "Estimated Cerebral Metabolic Rate of Oxygen in Severely Brain–injured Patients: A Valuable tool for Clinical Monitoring" (1995) *Critical Care Medicine* 23:66–70.

Pamela Sikes et al., "Jugular Bulb Oxygen Saturation Monitoring for Evaluating Cerebral Ischemia", *Crit Care Nurs Q* (1994) 17:9–20.

Mogens Jakobsen et al., "Retrograde Catheterization of the Right Internal Jugular Vein for Serial Measurements of Cerebral Venous Oxygen Content" *Journal of Cerebral Blood Flow and Metabolism* (1989) 9:717–720.

Carl–Henrik Nordstrom et al., "Cerebral Blood Flow, Vasoreactivity, and Oxygen Consumption During Barbiturate Therapy in Severe Traumatic Brain Lesions" *J Neurosurg* (1988) 68:424–431.

Julio Cruz et al., "Cerebral Blood Flow and Oxygen Consumption in Acute Brain Injury with Acute Anemia: An Alternative for the Cerebral Metabolic Rate of Oxygen Consumption?", *Critical Care Medicine* (1993) 21:1218–1224.

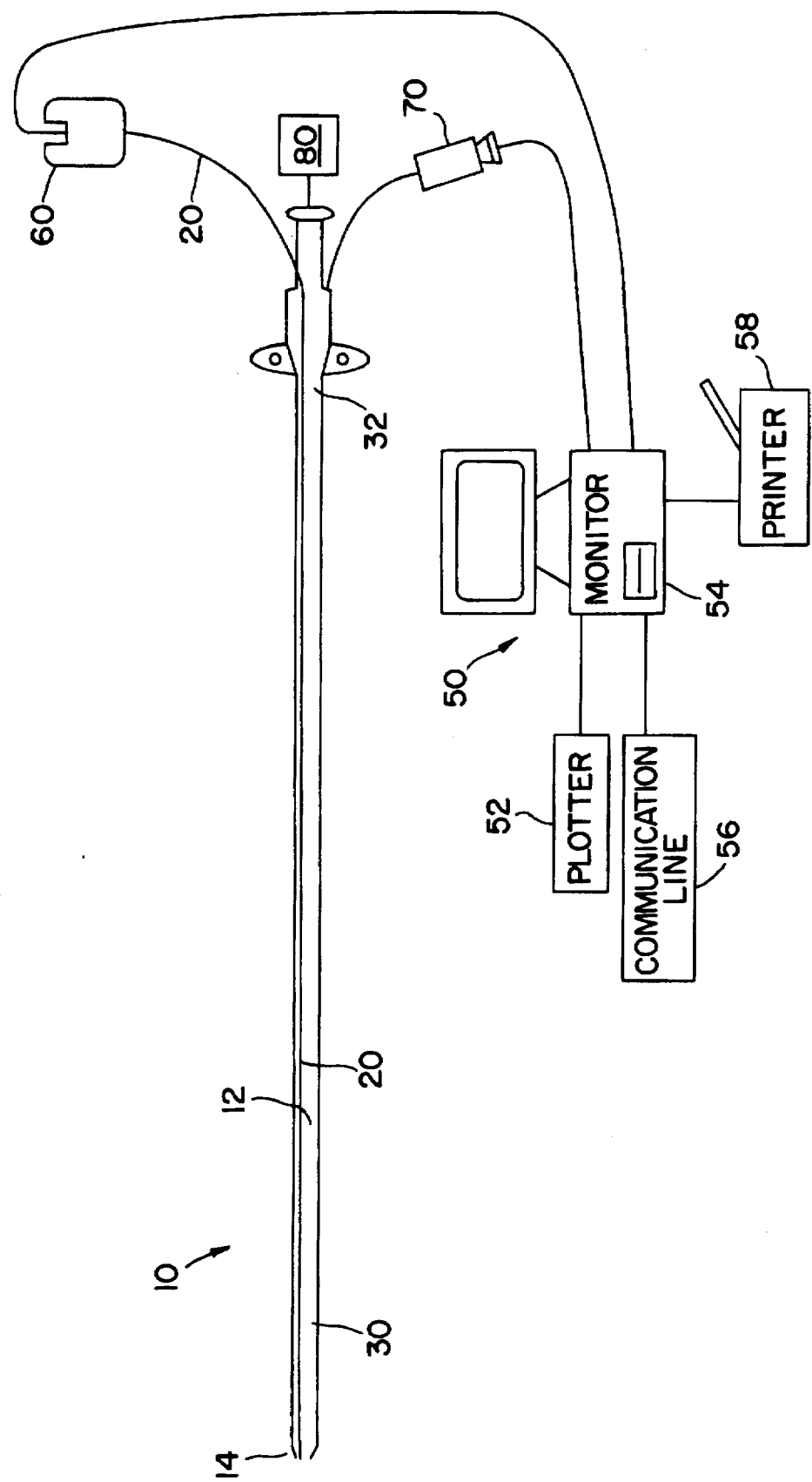

CEREBRAL HEMODYNAMIC MONITORING SYSTEM

FIELD OF THE INVENTION

The present invention relates to a novel hemodynamic monitoring system, more particularly a cerebral hemodynamic monitoring system.

BACKGROUND OF THE INVENTION

Cerebral blood flow and oxygen consumption are important parameters of the well-being of the brain under acute conditions. As such, the ability to monitor these physiological variables is useful in the management of critical care patients, particularly those suffering from severe head injury or cerebral ischemia. However, prior art methods of measuring jugular blood flow and oxygen consumption are complicated, utilize expensive equipment, demand specially skilled personnel to perform and necessitate patient transport to a special testing area. Hence, they cannot be repeated at reasonable intervals and, therefore, are of limited use in guiding treatment.

One prior art technique for quantitative assessment of cerebral hemodynamics is the Nitrous Oxide Elimination technique. This technique was developed by Kety and Schmidt fifty years ago (Kety, S. S. and Schmidt, C. F. (1945) Am. J. Physiol. 143: 53–65). In this technique, nitrous oxide gas is inhaled by the patient, and repeated measurements are made of nitrous oxide levels in the jugular blood. Analysis of the resulting elimination curve enables calculation of cerebral blood flow. However, this technique is cumbersome, expensive to perform, and requires specially trained personnel. Typically, in order to perform this technique at the patient's bedside nitrous oxide gas must be delivered outside the operating room, the only place in the modern hospital in which nitrous oxide is normally dispensed. Special mixing equipment which can deliver a steady concentration of nitrous oxide gas is usually employed. Additionally, in order to prevent contamination of the surrounding atmosphere and inhalation by the staff of nitrous oxide gas, a scavenging system is typically added to the patient ventilator. In order to measure cerebral hemodynamics, a catheter is typically placed in the jugular vein for acquisition of multiple blood samples followed by rapid delivery of the blood to a special device that can measure nitrous oxide concentration in the blood. This combination of factors makes the nitrous oxide elimination technique difficult to perform repeatedly in a manner that would enable it to be an integral part of patient care.

A second prior art technique for measuring cerebral hemodynamics is the Xenon Elimination Technique. This technique utilizes radioactive $Xe^{133}$, which is injected into the patient's blood. Special electrodes are placed around the patient's head, and the concentration of $Xe^{133}$ is measured over time. As in the Nitrous Oxide Elimination technique, an elimination curve is generated which enables calculation of cerebral blood flow. Current safety protocols typically call for the patient to be taken to a specially designed site where the radioactive material can be delivered without the hazard of environmental contamination. This technique also usually requires specially trained personnel to perform the test and the calculations. Furthermore, in the interest of limiting the patient's exposure to radiation, this technique may not be repeated as many times or as often as would otherwise be deemed necessary. This and the other factors noted above render this technique difficult to perform repeatedly. Thus Xenon Elimination Technique, like the Nitrous Oxide Elimination Technique, is extremely burdensome to incorporate into a standard regimen of patient management under normal clinical conditions.

A third prior art technique for measuring cerebral hemodynamics utilizes the Webster Coronary Sinus Retrograde Thermodilution Catheter, developed by Berré and Mélot (Berré, J., et al. (1994), in Yearbook of Intensive Care and Emergency Medicine 1994, ed. by J.-L. Vincent, pp 646–654). This catheter is the first tool that allows measurement of jugular blood flow at the bedside. It is a catheter that was originally designed to be used during open heart surgery in order to measure venous blood flow in the coronary sinus. This catheter, when placed in the jugular vein, enabled Berré and Mélot to perform measurement of jugular blood flow using the retrograde thermodilution technique. (Ganz, W., et al. (1971) Circulation 44: 181–195; Lagerkranser, M. et al. (1989) Acta Anaesthesiol. Scand. 33: 15–20). In this technique, a catheter incorporating two thermistors, one 25 mm and one 50 mm from the tip, is used. After insertion in the jugular bulb of the patient, body temperature ($T_B$) is recorded from the catheter thermistors . . . . Then, room temperature indicator (D5W or isotonic saline) is infused through the distal lumen in the jugular bulb using a constant infusion pump. The catheter thermistors measure the temperature of the blood-indicator mixture at 25 mm ($T_{M\text{-}distal}$) and 50 mm ($T_{M\text{-}proximal}$) from the tip of the catheter. A separate thermistor measures the temperature of the indicator ($T_I$). Flow at the distal or proximal site is calculated using the specific value of $T_M$ in the formula:

Flow (mL/min)=$(T_M-T_I)/(T_B-T_M) \cdot F_I$(mL/min)$\cdot$C where $F_I$ is the indicator flow rate (38.2 mL/min) and C a constant based on the thermal properties of blood and indicator (1.08 for D5W or 1.10 for isotonic saline).

(Berré, J., et al. (1994), pp 650–651) While this prior art technique is useful for measuring cerebral hemodynamics at the patient's bedside, there are many limitations associated with this technique.

First, the Webster catheter was designed to be placed directly into the coronary sinus in the heart by the surgeon. Insertion into the jugular vein can be performed via a cutdown or using a percutaneous introducer kit. Second, the catheter has a diameter of 7 French at the tip, and grows to 8 Fr 15 cm from the tip. As a result it typically can stay inside the small jugular vein a very limited period of time. To date the average placement time for this catheter is 1–3 hours. Furthermore, as used by Berré and Mélot, and by Cruz et al. (1995 Crit. Care Med. 23: 1412–1417), this technique involves the injection of 17 cc of fluid in 30 seconds for each test. Over a relatively short period, a number of these tests will infuse enough fluid into the patient's vasculature to significantly affect the patient's fluid volume. Finally, the catheter lacks a fiberoptic component to allow measurement of hemoglobin saturation. Thus this catheter is not usually appropriate for measurement of cerebral oxygen consumption.

Therefore, in view of the prior art deficiencies in measurement of cerebral blood flow and oxygen consumption, it should be apparent that, prior to the present invention, there existed a need in the art for an improved method of chronically measuring these important variables.

OBJECTS OF THE INVENTION

Accordingly, an object of the present invention is to provide a method for continuous and prolonged measurement of cerebral blood flow and oxygen consumption at the patient's bedside, using a simple measuring device that can be used in the critical care unit, and which requires minimal training to perform. This technique enables use of these important parameters in a clinical setting to affect patient management and care.

With the foregoing and other objects, advantages and features of the invention that will become hereinafter apparent, the nature of the invention may be more clearly understood by reference to the following detailed description of the preferred embodiments of the invention and to the appended claims.

SUMMARY OF THE INVENTION

In light of the foregoing objects of the invention, the present invention provides a jugular catheter that incorporates the technology of retrograde thermodilution and oximetry.

The present invention also provides an easy, percutaneous, over-wire insertion technique that may be easily mastered by clinical personnel.

The present invention further provides a jugular catheter of sufficiently small size to prevent disturbance of blood flow when inserted, enabling the catheter to remain inserted for days at a time.

The present invention further provides a system for continuous monitoring of cerebral oxygen extraction and frequent (more than 10 times per hour) measurements of cerebral blood flow. The combination of these two measurements allows for constant monitoring of cerebral metabolic rate; it thus can be used as an integral part of patient management and care.

The present invention further provides an automated system capable of performing continuous, automated data acquisition once the catheter has been placed, allowing measurements to be made without the need for specially trained personnel.

BRIEF DESCRIPTION OF THE DRAWING

The drawing illustrates a cerebral hemodynamics catheter in accordance with the present invention.

DETAILED DESCRIPTION

The present invention provides a flexible, easily insertable cerebral hemodynamics monitoring system that allows for continuous oximetry, measurement of blood pressure and venous blood flow, and repeated blood sampling.

The cerebral hemodynamics monitoring device of the present invention, as shown in the figure, comprises a catheter 10 having a length sufficient to extend from an insertion point to the jugular bulb, which in an adult is about 18–20 cm. The length of the catheter is preferably 18 cm. The outer diameter of the catheter 10 is less than the inner diameter of a jugular vein to allow blood flow around the catheter, which permits long term use of the system. The outer diameter of the catheter 10 is in a range of 4.5–5.5 Fr, with a diameter of 4.5 Fr being preferred. The inner main lumen 12 of the catheter 10 is preferably in a range of 4–5 Fr, more preferably 4 Fr.

The catheter 10 may be composed of a material which is substantially rigid at room temperature and during insertion, and which softens at body temperature to become pliant. The catheter 10 is preferably opaque to X-rays, and may be marked at the tip 14 for easy visualization using conventional X-ray equipment. The catheter 10 preferably comprises an optic fiber 20 for measurement of oxygen saturation, the optic fiber 20 being capable of transmitting at least two wavelengths of light. The catheter 10 preferably further comprises a first thermistor 30 positioned not more than about 25 mm from the tip of the catheter, and preferably 25 mm from the tip. The catheter 10 also preferably comprises a second thermistor 32, located preferably at an entry to the catheter.

The catheter 10 of the present invention may be inserted over a guide wire using the Seldinger technique: the guide wire is inserted into the vein and positioned accurately within the lumen of the jugular vein; the catheter is then passed over the guide wire into the vein. The guide wire is preferably longer than the catheter, more preferably in a range of 40–45 cm long, most preferably 40 cm long, and has a diameter preferably less than 0.025". The guide wire also preferably has a soft tip.

The monitoring device of the present invention also comprises a computerized cerebral hemodynamics monitor 50 that includes means 60 for continuous jugular oximetry ($S_jO_2$, %), arterial pulse oximetry ($S_aO_2$, %), and means 70 for measurement of jugular blood flow (JBF, ml/min/100 g tissue), preferably via retrograde thermodilution. Based on these measurements, the computerized cerebral hemodynamics monitor 50 of the present invention also allows for continuous calculation of cerebral $O_2$ extraction ($CEO_2$, %), cerebral $O_2$ consumption ($CMRO_2$), and cerebral vascular resistance (CVR), preferably using the following formulae:

$$CEO_2 = SaO_2 - SjO_2$$

$$O_2 \text{ Extraction Ratio} = (CEO_2 / S_aO_2) \bullet 100$$

$$\text{Jugular Blood Flow (JBF; ml/min)} = (T_M - T_I)/(T_B - T_M) \bullet F_I(\text{ml/min}) \bullet C$$

wherein $T_M$=Temperature measured
$T_I$=Temperature of injectate
$T_B$=Body temperature
$F_I$=Injectate flow rate (ml/min)
C=a constant based on the thermal properties of blood and indicator (1.08 for D5W or 1.10 for isotonic saline).
CBF=JBF• $2/13$ ml/min (per 100 g tissue)
$CMRO_2$=CBF•$CEO_2$•Hgb•1.39
Cerebral Vascular Resistance=[(MAP-JVP)/CBF]•1000 (dyne)

The device of the present invention may also provide means 52 for automated plotting of these parameters, and trends within these parameters, over time, and means 54 for storage of data, preferably on 3.5" floppy disks. The monitor 50 of the present invention preferably includes a link 56 for communicating with typical hospital bedside monitors, personal computers, and/or other computer systems. An example of a monitor suitable for use in the present invention is the Explorer™ Continuous Cardiac Output and Oximetry Monitor (Baxter Healthcare Co., Edwards Critical Care Division).

The device according to the present invention may also provide a programmable injectate infusion pump 80 that provides for background flow, planned interval boluses, and PRN bolus capability. The pump 80 preferably controls background flow rate in ml/hour, interval and PRN bolus flow rate in ml/minute or cc/measurement; inter-test interval may be set in minutes; lock-out time may be set in minutes. Finally, the pump 80 preferably has the capability of recording and storing infusion history, including number of injections, planned/PRN boluses, and total volume injected. An example of a pump suitable for use in the present invention is the Baxter AS40 A infusion pump.

The monitoring device also includes a printer 58, attached to the monitor 50, that is preferably capable of printing the screen display from the monitor, the last day's history, the case history and summaries, and trends and diagrams. An example of a printer suitable for use in the present invention is the Oximetrix™ 3 printer (Abbott Critical Care Systems).

While the invention has been described and illustrated herein by reference to various specific materials, procedures and examples, it is understood that the invention is not restricted to the particular materials, combinations of materials, and procedures selected for that purpose. Numerous variations of such details can be implied and will be appreciated by those skilled in the art.

What is claimed is:

1. A cerebral hemodynamic monitoring system comprising:
    a jugular catheter provided with means for measuring jugular blood flow and means for measuring blood oxygen saturation;
    an independently regulatable infusion pump connected to an entry of the jugular catheter; and
    a computer data analysis and storage system connected to receive data from said means for measuring jugular blood flow and said means for measuring blood oxygen saturation for calculating cerebral $O_2$ extraction ($CEO_2$, %), cerebral $O_2$ consumption ($CMRO_2$), cerebral blood flow (CBF), and cerebral vascular resistance (CVR).

2. The cerebral hemodynamic monitoring system of claim 1, wherein the jugular catheter has a length sufficient to reach the jugular bulb in an adult.

3. The cerebral hemodynamic monitoring system of claim 2, wherein the jugular catheter has a length in a range of 18–20 cm long.

4. The cerebral hemodynamic monitoring system of claim 1, wherein the jugular catheter has an outer diameter less than an inner diameter of an adult vein to permit blood flow past the catheter.

5. The cerebral hemodynamic monitoring system of claim 4, wherein the jugular catheter has an outer diameter of 4.5–5.5 Fr, and an inner diameter of 4–5 Fr.

6. The cerebral hemodynamic monitoring system of claim 1, wherein the jugular catheter is 18 cm long, has an outer diameter of 4.5 Fr, and an inner diameter of 4 Fr.

7. The cerebral hemodynamic monitoring system of claim 1, wherein the jugular catheter is composed of a substance which is substantially rigid at room temperature and during insertion, and pliant at body temperature.

8. The cerebral hemodynamic monitoring system of claim 1, wherein the jugular catheter is opaque to X-rays, and is marked at the tip for easy visualization using conventional X-ray equipment.

9. The cerebral hemodynamic monitoring system of claim 1, wherein the means for measuring oxygen saturation comprises an optic fiber for measuring oxygen saturation.

10. The cerebral hemodynamic monitoring system of claim 9, wherein the optic fiber is capable of transmitting at least two wavelengths of light.

11. The cerebral hemodynamic monitoring system of claim 1, wherein said means for measuring jugular blood flow comprises a first thermistor located not more than 25 mm from a tip of the catheter, and a second thermistor located at an entry to the catheter.

12. The cerebral hemodynamic monitoring system of claim 11, wherein the first thermistor is located 25 mm from the tip of the catheter.

13. The cerebral hemodynamic monitoring system of claim 1, wherein the jugular catheter is insertable over a guide wire.

14. The cerebral hemodynamic monitoring system of claim 1, further comprising a guide wire having a length greater than a length of the catheter and disposed within an inner lumen of the catheter.

15. The cerebral hemodynamic monitoring system of claim 14, wherein the guide wire has a soft tip, and has a length in a range of 40–45 cm and a diameter less than 0.025".

16. The cerebral hemodynamic monitoring system of claim 14, wherein the guide wire is 40 cm long.

17. The cerebral hemodynamic monitoring system of claim 1, wherein the computer data analysis and storage system comprises:
    a computer for analyzing data received from said means for measuring oxygen saturation and said means for measuring blood flow;
    means for displaying raw and processed data;
    means for printing raw and processed data; and
    means for storing raw and processed data.

18. A cerebral hemodynamic monitoring system comprising:
    a jugular catheter;
    means for measuring jugular blood flow attached to the jugular catheter;
    means for measuring blood oxygen saturation attached to the jugular catheter;
    an independently regulatable infusion pump connected to an entry of the jugular catheter; and
    a computer data analysis and storage system connected to receive data from said means for measuring blood flow and said means for measuring oxygen saturation and calculating cerebral $O_2$ extraction ($CEO_2$, %), cerebral $O_2$ consumption ($CMRO_2$), cerebral blood flow (CBF), and cerebral vascular resistance (CVR), wherein said means for measuring jugular blood flow is a retrograde thermodilution device.

19. A method for monitoring cerebral hemodynamics with a system a jugular catheter comprising means for measuring blood flow and means for measuring oxygen saturation, an independently regulatable infusion pump connectable to the jugular catheter, and a computer data analysis and storage system connected to receive blood flow and oxygen extraction data from the jugular catheter, the method comprising the steps of:
    a) inserting the jugular catheter in a patient;
    b) introducing an infusion liquid in the catheter;
    c) collecting data on blood flow and oxygen saturation with the catheter;
    d) analyzing said data with the computer data analysis system to obtain cerebral $O_2$ extraction ($CEO_2$, %), cerebral $O_2$ consumption ($CMRO_2$), cerebral blood flow (CBF), and cerebral vascular resistance (CVR);
    e) providing analyzed data in a comprehensible form; and
    f) repeating steps b through e as needed.

20. The method according to claim 19, further comprising the step of storing the analyzed data obtained in step d, and wherein the step of providing analyzed data includes retrieving and providing previously stored data.

21. A jugular catheter usable in a cerebral hemodynamic monitoring system, said catheter comprising:
    a catheter shaft including at least one through lumen;

at least one sensor attached to said catheter shaft for obtaining data that permits measurement of jugular blood flow;

at least one sensor attached to said catheter shaft for obtaining data that permits measurement of blood oxygen saturation;

wherein said catheter shaft is sized and configured to permit fluid to be injected at a frequency of at least ten times per hour through said at least one through lumen into a patient's jugular vein in which said catheter shaft has been inserted for a continuous and prolonged time.

22. The method according to claim 19, wherein said step of repeating steps "b" through "e" as needed is performed at a rate of at least ten times per hour.

* * * * *